(12) United States Patent  
Lipson et al.

(10) Patent No.: US 7,742,166 B2
(45) Date of Patent: Jun. 22, 2010

(54) ENHANCING SELECTIVITY AND/OR SENSITIVITY OF SPECTROSCOPIC MEASUREMENTS IN MEDIA

(75) Inventors: Jan Lipson, Cupertino, CA (US); Albert L. Lipson, Cupertino, CA (US); Robert P. McNamara, San Jose, CA (US)

(73) Assignee: C8 Medisensors Inc., San Jose, CA (US)

( * ) Notice: Subject to any disclaimer, the term of this patent is extended or adjusted under 35 U.S.C. 154(b) by 439 days.

(21) Appl. No.: 11/740,767

(22) Filed: Apr. 26, 2007

(65) Prior Publication Data

US 2007/0285655 A1 Dec. 13, 2007

Related U.S. Application Data

(60) Provisional application No. 60/796,012, filed on Apr. 27, 2006.

(51) Int. Cl.
*G01J 3/00* (2006.01)
(52) U.S. Cl. ........................................ 356/300; 356/301
(58) Field of Classification Search ................. 356/300, 356/301
See application file for complete search history.

(56) References Cited

U.S. PATENT DOCUMENTS

| 5,553,616 | A | 9/1996 | Ham et al. |
| 6,144,791 | A | 11/2000 | Wach et al. |
| 6,862,090 | B2 | 3/2005 | Chen et al. |
| 2008/0129992 | A1* | 6/2008 | Matousek et al. ........... 356/301 |

OTHER PUBLICATIONS

PCT International Search Report and Written Opinion, PCT/US07/67608, Feb. 13, 2008, 8 pages.

* cited by examiner

*Primary Examiner*—L. G Lauchman
(74) *Attorney, Agent, or Firm*—Fenwick & West LLP

(57) ABSTRACT

An apparatus for enhancing the selectivity for spectroscopic measurements of analytes in a turbid medium is described. In one example, spatial filters are used to select only certain radii from the medium to be imaged. This selection is accomplished by placing an optical obstruction on the surface of the medium or at an image plane of the surface later in the optical imaging system. In one implementation, this is achieved by placing a fiber bundle at an image plane of the collecting optical system and then using a spacer of appropriate size at the center of the fiber bundle to act as a central obstruction.

9 Claims, 5 Drawing Sheets

ENHANCING SELECTIVITY AND/OR SENSITIVITY OF SPECTROSCOPIC MEASUREMENTS IN MEDIA

CROSS-REFERENCE TO RELATED APPLICATION(S)

This application claims priority under 35 U.S.C. §119(e) to U.S. Provisional Patent Application Ser. No. 60/796,012, "Enhancing Selectivity and/or Sensitivity of Spectroscopic Measurements in Media," filed Apr. 27, 2006, the subject matter of which is incorporated herein by reference in its entirety.

BACKGROUND OF THE INVENTION

1. The Field of the Invention

This invention relates to increasing the spatial selectivity and/or sensitivity of spectroscopic measurements, for example as can be used to make non-invasive measurements of analytes in biological organisms.

2. Background and Relevant Art

Many attempts have been made to create appropriate apparatus for the non-invasive measurement of significant substances within biological organisms. The importance of such measurement capability arises not only from the need to observe biochemical reactions in such organisms without disturbance to the system but also in order to help control chronic diseases such as diabetes, where it is highly desirable to measure the patients blood glucose levels much more frequently than is practical, when puncturing the skin is required. Molecular spectroscopy has been proposed to make such measurements; however, the blood and interstitial fluids contain a very great number of compounds which must be distinguished. Absorption spectroscopy in the visible or near infrared suffers from the difficulty that the spectrum of many compounds that are present in the blood and other tissues substantially overlap in this region. Mid-IR spectroscopy produces spectra which are considerably more unique to individual molecules but suffers from two serious problems: (1) Detectors must be operated at very cold temperatures if they are to be sufficiently sensitive and (2) Water absorbs mid-IR radiation very strongly and such radiation can only penetrate a few tens of microns into an organism.

Raman spectroscopy has been proposed to obviate some of these difficulties. In Raman spectroscopy a scattering spectrum is produced, at frequencies which are at the difference of the input radiation, and the characteristic spectral frequencies of the molecule. The resulting spectral signatures are advantageously particular to the analytes of interest. However, the cross-sections for Raman scattering are very small, and the resulting signals are very weak. Weak signals can also arise from spectroscopies that use other non-linear processes, or where the available power from the light source is small. Other representative examples would include four wave mixing, frequency doubling, and multiphoton fluorescence.

The difficulties arising from the weakness of the signal can be greatly exacerbated if the analyte of interest is primarily located at some depth away from and/or below the surface of the sample, and if the sample otherwise produces a large amount of scattering of the optical signal (turbid medium). A further complication arises when the material, which comprises the layers that are near the surface, consists of compounds whose spectra have substantial overlap with that of the analyte. Even if the aperture of the optical system which collects the light is large, the signal of interest may be dominated by the compounds near the surface, and the signal produced by the analyte will be obscured. A large optical aperture for the system will inevitably give rise to large optical collecting elements such as lenses or mirrors whose function is to separate light having a multiplicity of optical wavelengths into its constituent spectral components. The size of and cost of the whole apparatus will therefore scale positively with the aperture size.

BRIEF SUMMARY OF THE INVENTION

These and other limitations are addressed by the present invention, in which unwanted signals are reduced by spatially filtering, thus increasing the selectivity of and/or sensitivity to the desired spectral signals.

For example, one embodiment of the invention can be used to make a calibrated measurement of analytes in samples. The sample is illuminated with light. The interaction which produces a scattering spectrum that is characteristic of the analyte of interest may be relatively weak in intensity, and the desired analyte to be measured is predominantly located remote from or some distance below the surface of the sample. In addition, there may be significant scattering from or around the surface of the sample that would obscure the spectrum of the analyte of interest. A spatial filter (e.g., central obscuration located in the relevant plane) is used to reduce the strength of the unwanted scattering. Therefore, the ratio of signals arising from significant depths to that arising from the surface is made larger.

In many cases, light scattered from near the surface of a turbid medium is more likely to be located near the center (i.e., along the optical axis) of the exciting optical beam whereas light originating from some depth is more likely to emerge from locations that are separated by some significant distance from the optical axis. In consequence, if a central obstruction is employed in the optical system, the light detected from surface scattering can be substantially suppressed while the light detected from scattering which emerges from some depth will be reduced to a substantially lesser degree.

The light which originates near the center of the optical beam need not be rejected entirely, but may be diverted to a spectroscopic analysis system and set of detectors different from those used to observe the light which originates at some substantial distance from the center. In that manner, the information which is obtainable from the scattered light at or near the optical axis is not lost. As an example, such information may be used to determine the concentration of substances whose spectra interfere with that of the analyte which is presumed not to be located near the surface. Therefore, by means of an appropriate algorithm, an appropriately weighted measure of the spectrum from the center may be subtracted from the spectra originating from non-central locations in order to remove the contribution from the interfering substances which may also be present at depth.

When a central obstruction is used as the spatial filter, it need not be physically located at the surface of the sample. For example, it could instead reside in a convenient image plane of the optical system which collects the scattered light.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims.

BRIEF DESCRIPTION OF THE DRAWINGS

In order to describe the manner in which the above-recited and other advantages and features of the invention can be obtained, a more particular description of the invention above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

Figure 1:
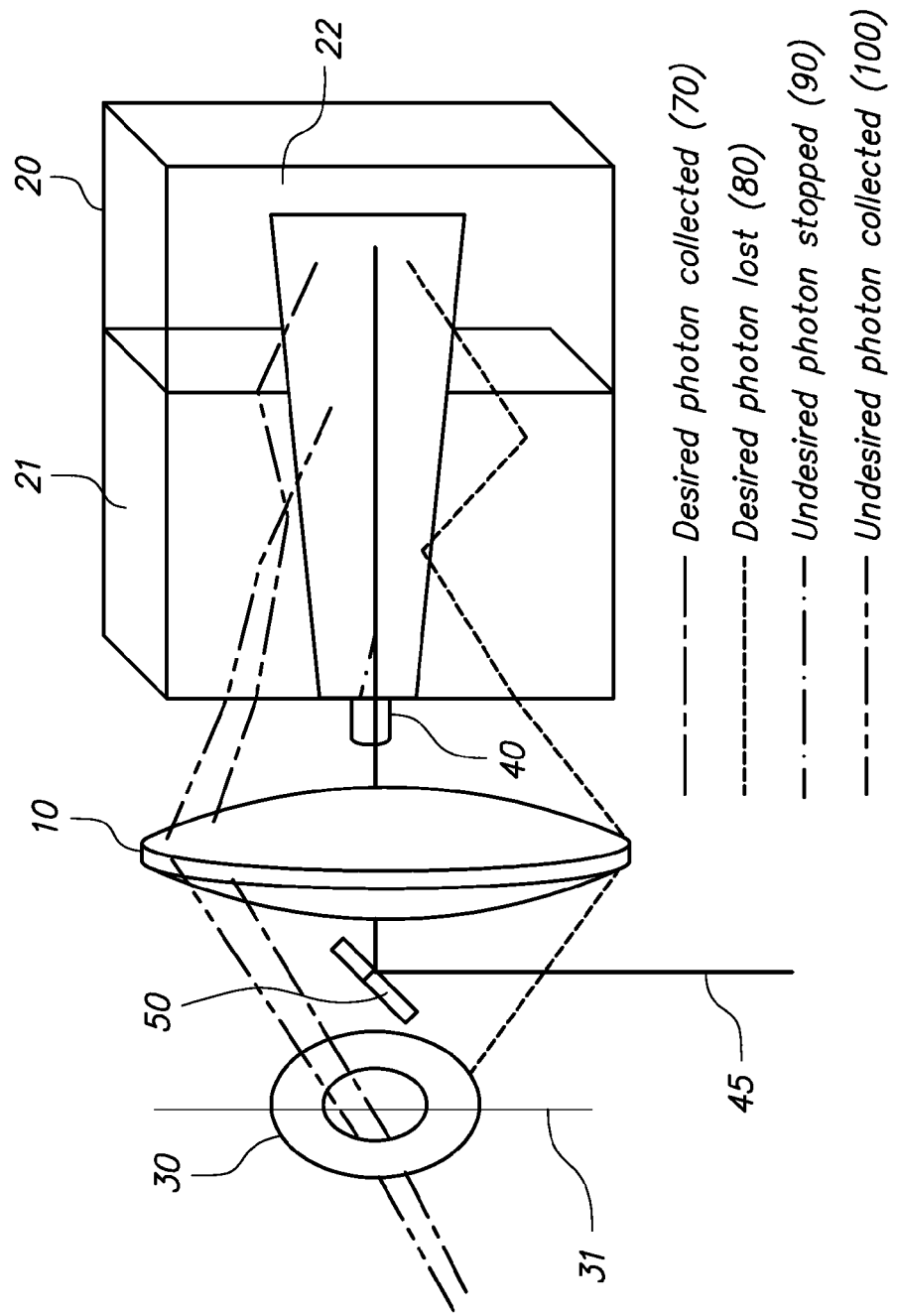
FIG. 1 shows the principle components of one of the preferred embodiments of the apparatus in relation to the sample, and shows the use of a central obstruction in rejecting unwanted scattering.

A diagram of one embodiment of the proposed apparatus is presented in FIG. 1. A laser beam 45 is brought to bear on a sample medium 20 through the use of a mirror 50. One could launch light 45 onto the sample medium 20 in other ways also. In order for the light 45 to impinge on the sample medium 20, the light passes through a spatial filter 40, which is an obstruction shaped as an annulus with a small hole, approximately the size of the laser beam 45, through which the laser beam passes. In the preferred embodiment, the annular obstruction is thin so to a first order approximation the thickness of the obstruction does not affect the following description. The size and shape of the obstruction 40 is designed to weight the contribution from surface scattering relative to scattering that occurs at various depths within the sample medium, as described below.

The light 45 then passes through the annular obstruction 40 and impinges upon the sample medium 20. Once the laser beam 45 passes into the sample medium 20, it is scattered and absorbed at various depths within the medium. In this example, the sample medium 20 includes two regions 21 and 22. Region 21 is encountered by the laser beam 40 first but it is not the region of interest. For example, region 21 may include analytes other than the analytes of interest. Region 22 is the region that contains the analytes of interest. For convenience, photons generated by region 21 will be referred to as "undesired photons" (even though they may actually be desirable for certain purposes) and those generated by region 22 will be referred to as "desired" photons.

Some of the inbound laser light 45 is absorbed and back scattered quite close to the surface of region 21, as is shown by undesired photon 90. Much of the back-scattered light 90 that is re-emitted near the point of incidence of the laser beam is rejected by the optical obstruction 40. Back-scattered light 90 that is scattered back along the path of the laser beam 45 may propagate through the pinhole, in which case it intersects mirror 50 and is deflected away from the detector collection optics.

Photon 100 represents another undesired photon that is being backscattered from region 21. However, unlike photon 90, the depth at which photon 100 is scattered coupled with its angle of scattering and its radial off axis position allows this photon to be collected by the imaging lens 10 and focused on the image plane 31 contained within aperture 30. The ability of a photon from the sample medium 20 to be transferred to the image plane 31 will be a function of the size of lens 10.

Photon 70 represents a scattered photon from the desired region 22 that is collected at image plane 31. The ability of the system to collect photon 70 from region 22 will be dependent upon the depth at which photon 70 is scattered coupled with its angle of scattering and its radius off axis. Photon 80 is another photon from the desired region 22. However, due to its depth, angle of scattering, radius off axis and subsequent scattering, it is lost due to impinging upon aperture 30. The ability of the optical system to collect scattered light that is within the radius and angle combinations of the lens that then can be imaged through an appropriate aperture and into the rest of the optical system will be a strong function of the size (radius) of obstruction 40.

Figure 3:
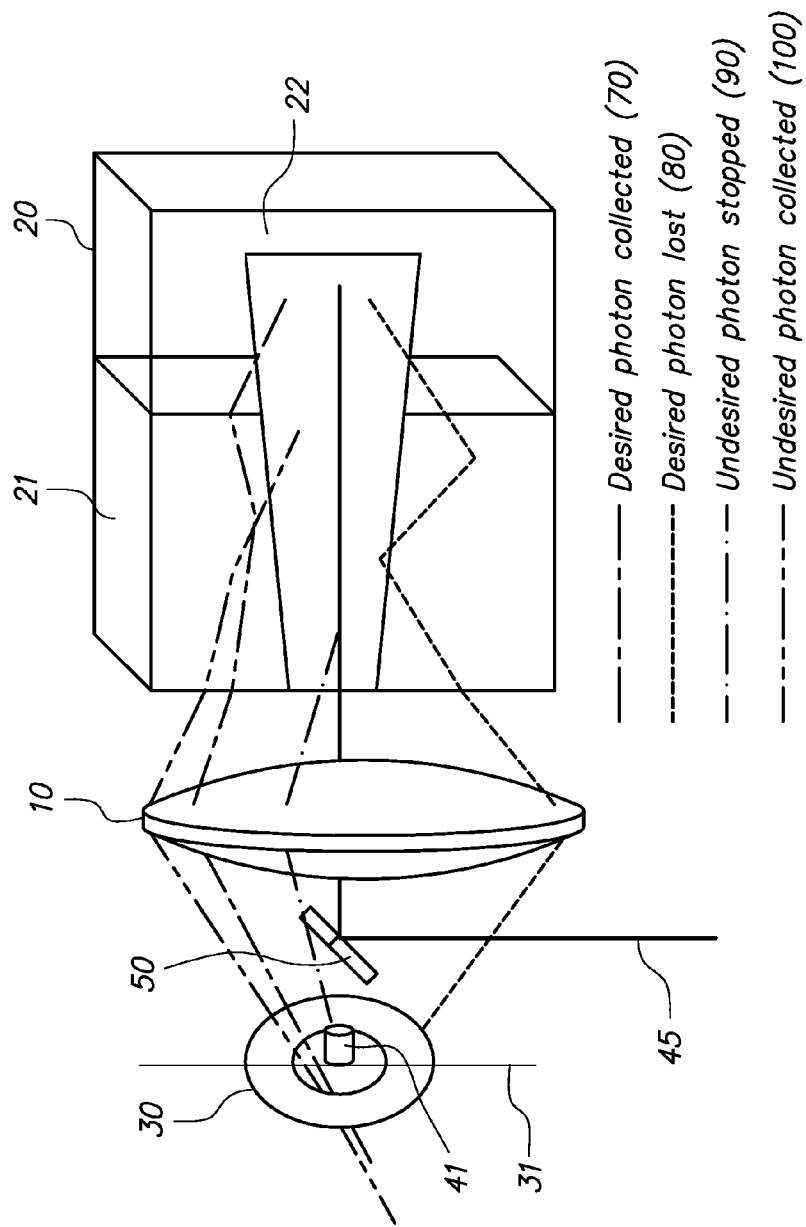
FIG. 3 shows a preferred embodiment in which the central obstruction is placed in the image plane of an appropriate focusing optic.

A second preferred embodiment is shown in FIG. 3. This example is similar to FIG. 1 but the optical obstruction 41 is placed in the image plane within aperture 30. Optical obstruction 41 differs from optical obstruction 40 in that it is solid as opposed to being annular in shape, given there is no requirement to pass laser light through the optical obstruction. As in FIG. 1, a laser beam 45 is brought to bear on a sample medium 20 through the use of a mirror 50. The light then is presumed to scatter and be absorbed inside the tissue. Some of the light will be re-emitted from the surface. Some of the inbound laser light is absorbed and back scattered quite close to the surface and is shown as photon 90. The back scattered light 90 that is reemitted near the incidence of the laser beam is imaged by lens 10 on the image plane 31 defined be the area within aperture 30 but is rejected by the circular optical obstruction 41 on the image plane. Back-scattered light 90 that is scattered back along the optical axis is seen to intersect the mirror 50 and is deflected away from the detector collection optics. Photons 70, 80 and 100 are collected or rejected the same as in FIG. 1.

Light that is within the radius and angle combinations of the lens can be imaged. Some of the light is then obstructed by an optical obscuration at an image plane. This obstruction is central in respect to the optical axis of the system. This gives the same effect on the light as the obscuration as in the apparatus in FIG. 1. The advantage of this methodology is to put the obscuration at a more convenient point in the optical system. This allows for the laser beam to reach the skin unimpeded by an obscuration.

The characteristic that makes this apparatus useful in allowing for depth selectivity is the radial distributions of light that is reemitted from different depths. This characteristic can be simulated by using a Monte Carlo simulation, which tracks the progress of a number of photons through a scattering (turbid) medium with absorption.

The simulation uses individually tracked photons that follow the rules for scattering and absorption.

$$\% \text{ Absorption} = e^{-\frac{l}{l_o}} \tag{1}$$

where l is the path length of the photon, and $l_o$ is the absorption length of the medium where the light is traveling. The simulation tracks the photon in steps and removes a given weight from the photon dependent on its path length for a given step. This enhances the efficiency of the program versus using a purely statistical approach, where a probability for complete absorption is used.

Scattering is handled through the use of a probability of a scattering event occurring over a given path length. The simulation calculates this based on a constant of the medium called the scattering coefficient. When the program determines a scattering event should occur, it randomizes the direction of the photon.

Figure 2:
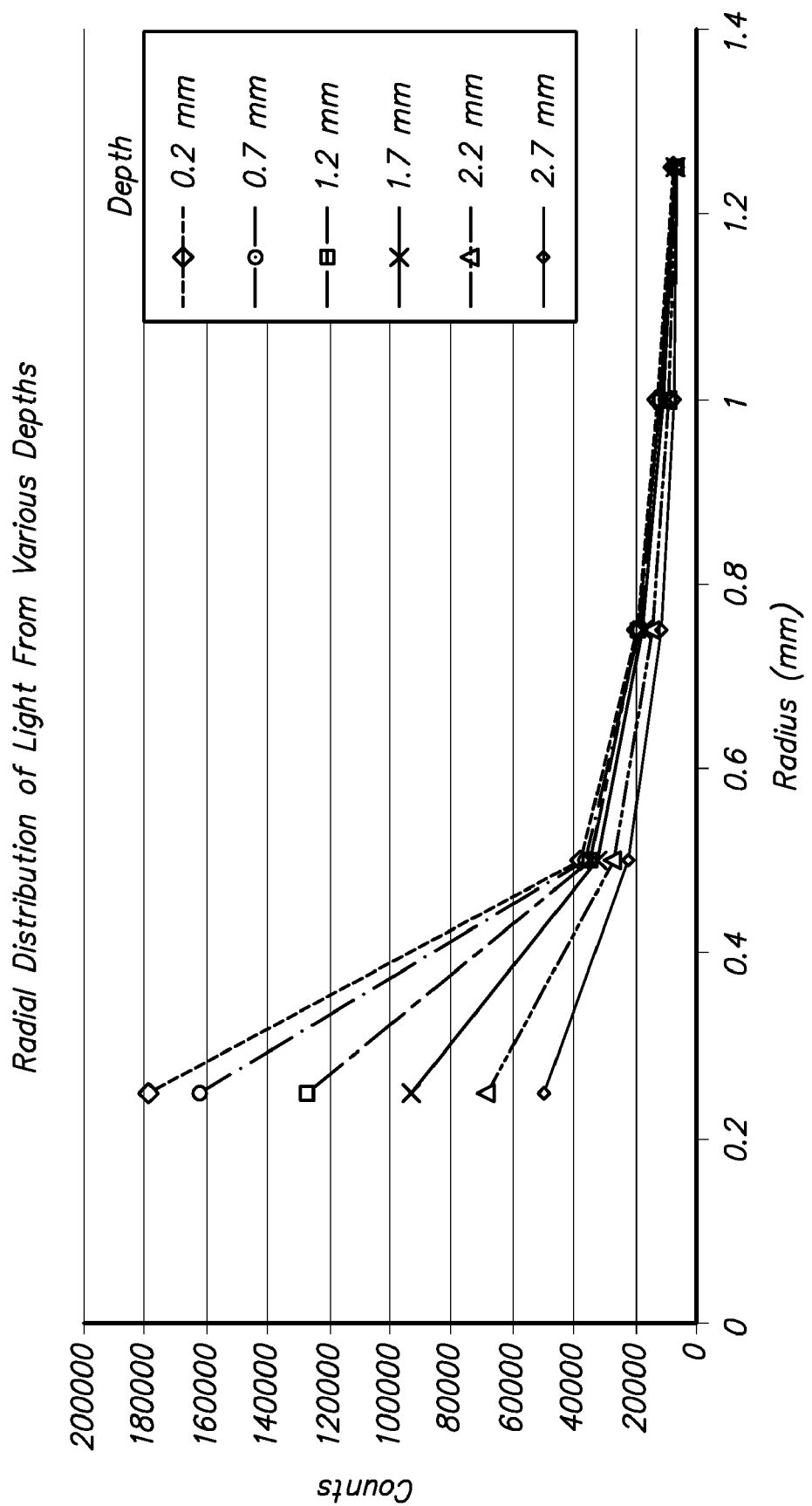
FIG. 2 is a graphical representation of the output of a Monte Carlo simulation for the scattering of photons in a turbid medium with absorption showing the collection of light which is scattered at various depths as a function of the radius from the exciting laser beam at which the light emerges.

The simulation was used in a fashion that where an absorption event occurred a photon was reemitted at the same position as it was absorbed at a random angle. This was to model the phenomenon of Raman signal being produced. Any light that would be scattered back out of the tissue could be ignored because its wavelength would not change and could be rejected by the use of a wavelength selective optical device such as a filter or diffraction grating and aperture. The light that was reemitted from the absorption events could then be tracked by depth range. If this light is absorbed it can be ignored, because a second absorption event would likely destroy any photons generated through the Raman Effect. Then any photons that reach the surface are recorded based on their radial positions into bins. A pattern emerges that as the depth increases the signal decreases but also the radial distribution becomes wider. This trend can be seen in FIG. 2. From the graph it is easy to see that for small radii (less than about 0.5 mm) the shallower depths have the largest signal. At larger radii, the difference between the shallow and deep depth signals becomes smaller. At the highest radii examined, the signals are almost equivalent.

These distributions show that if only light from a given set of radii are utilized the ratio of desirable light to undesirable light can be improved. This ratio is important because the undesirable signal contributes to the shot noise of the system as well as possible overlapping lines. The shot noise is a random deviation of the signal with root mean square of the amplitude equal to the square root of the signal. Therefore, as the broadband signal from the undesirable regions is reduced, the noise decreases. This noise makes it hard to determine signal strength and if the signal is small finding the desired signal can be difficult.

Once a given size of lens is chosen based on the needs of cost and space as well as the speed of the lens, this coupled with the depth of the desired sample in the medium can be used to determine the most desirable radii. Then an obstruction coupled with an aperture can be used to only admit the radii desired. This type of obstruction and aperture structure can be placed on the surface of the medium or at an image plane in the optical system.

This system can also be designed to remove any specular reflection. A specular reflection is produced whenever light passes through an interface between two media with different indices of refraction.

$$\Gamma = 100(n_1 - n_2)^2 / (n_1 + n_2)^2 \quad (2)$$

where $\Gamma$ is the percent reflectance, $n_1$ and $n_2$ are the respective indices of refraction of the two mediums the light is traveling between. The light will be eliminated by the central obstruction because the light will be coming from the same spot as the laser. Any angle, which it is reflected, will be eliminated. The importance of this is to attempt to eliminate excess laser radiation from entering the spectrometer. This reduces any anomalies in the laser as well as minimizing the requirement for laser line rejection. Excessive laser light usually should not be allowed to reach the spectrometer because the diffraction process it uses is not perfect and will leave some broadband signal from the input of a single wavelength of light, which will result in an increase in the noise.

Figure 4:
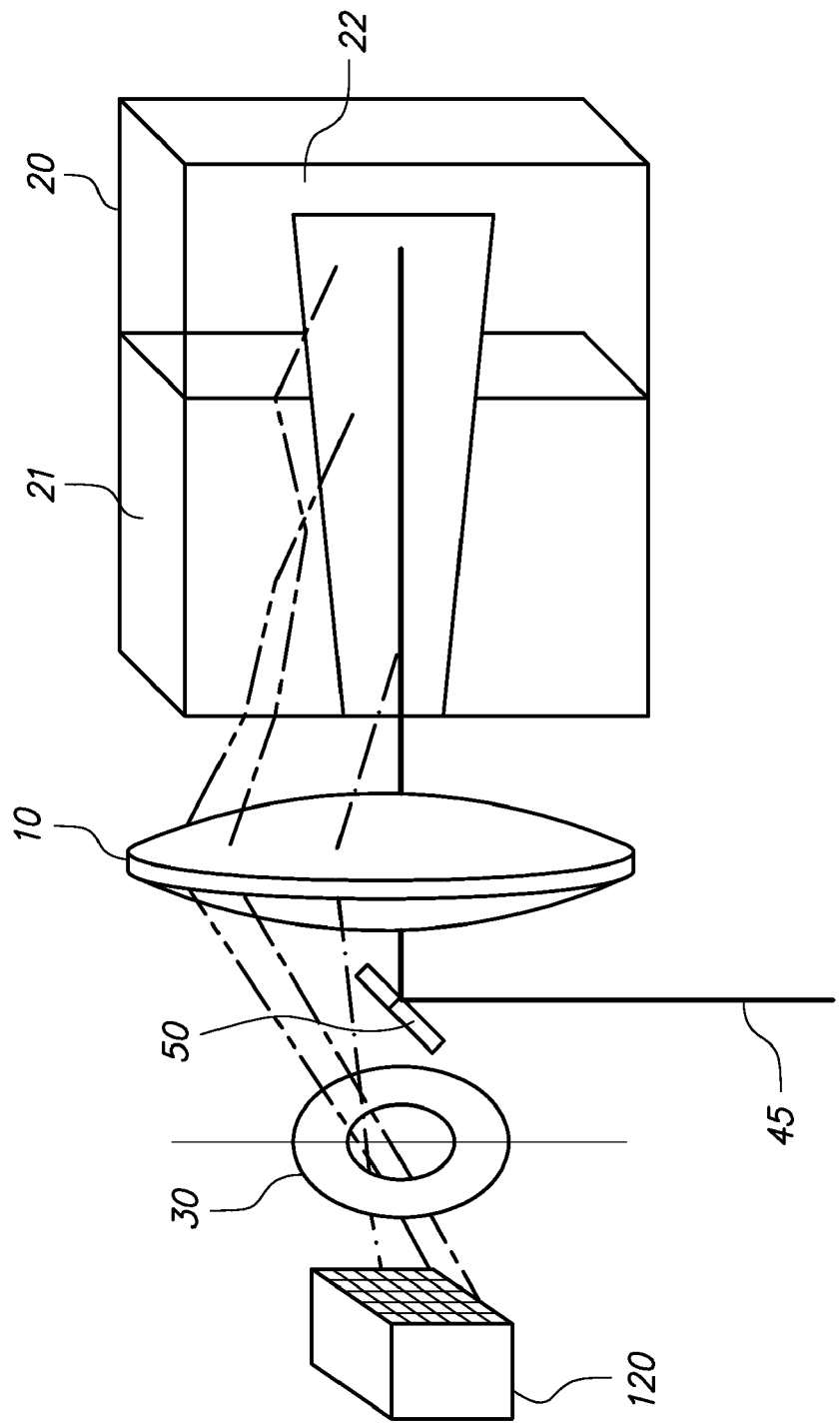
FIG. 4 shows an alternative version of the preferred embodiment in which separation of the light from the central and more remote radii is achieved by use of a multiplicity of detectors.

The central light that may be undesirable does not necessarily need to be absorbed by an obstruction. For example, this light can be diverted to a separate detection system by use of a mirror or other routing tool. Another variation is to let the light hit a detector 120 with spatial resolution as shown in FIG. 4. This allows separation of the light spatially from the detector while retaining possibly useful elements of the signal for analysis.

Figure 5:
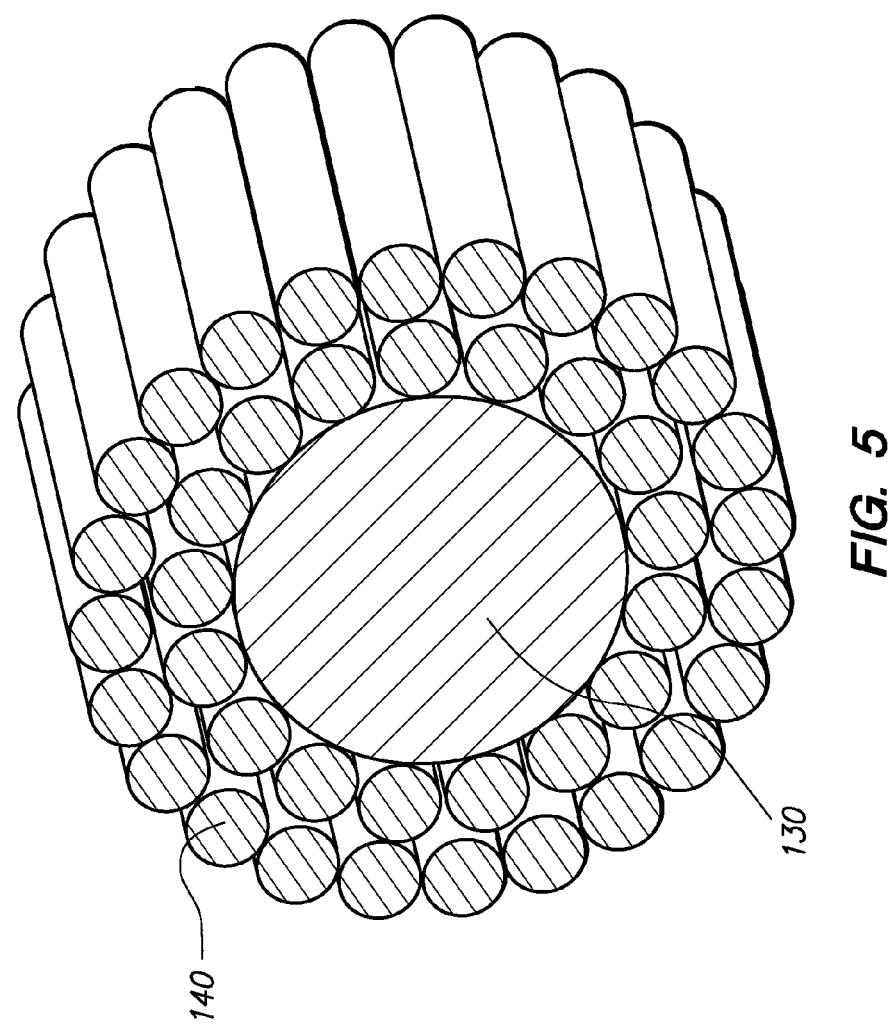
FIG. 5 shows an alternate version of the preferred embodiment in which a fiber bundle is used to collect light in the image plane and where a spacer that acts as an obstruction has been placed at the central location of the fiber bundle.

Another way of placing an obstruction (or other spatial filter) in the image plane of the optical system is shown in FIG. 5. In this embodiment, a fiber bundle is used to collect light from the optical system and then transfer a circular pattern from the image plane to a vertical slit type for use in a spectrometer. Normally the fiber bundle is placed at an image plane. In this fiber bundle, a number of fibers 140 are placed in a circular type pattern as shown in FIG. 5. In this figure a spacer 130 has been placed at the central location of the fiber bundle. This then allows the fiber bundle to only collect light in a given set of radii. This is a convenient method of employing this type of enhancement. Alternately, fibers can occupy the central location but the collected light treated differently.

The invention claimed is:

1. An apparatus for enhancing spectroscopic measurements of one or more analytes in a sample, the apparatus comprising:
   optics that collect light scattered from a sample illuminated by a source of optical radiation, the sample containing one or more analytes;
   a spatial filter positioned to reduce the strength of light scattered from or around a surface of the sample and collected by the optics;
   a spectroscopic apparatus positioned to receive the scattered light collected by the optics, that divides the received light according to wavelength; and
   one or more optical detectors that receive the wavelength-divided light from the spectroscopic apparatus.

2. The apparatus of claim 1, wherein the spatial filter is a central obscuration located in an image plane of the optics.

3. The apparatus of claim 2, wherein, at the surface of the sample, a diameter of the image of the source of optical radiation is less than a diameter of an image of the optical obscuration.

4. The apparatus of claim 2, wherein the central obscuration is an annular obscuration.

5. The apparatus of claim 1, wherein the sample is of biological origin.

6. The apparatus of claim 5, wherein the sample is human tissue.

7. The apparatus of claim 5, wherein the sample is human skin.

8. The apparatus of claim 1, wherein a first analyte of the analytes is substantially absent from and around a surface of the sample, and the light collected by the optics includes light scattered by the first analyte.

9. The apparatus of claim 1, further comprising the source of optical radiation, wherein a wavelength of the source is between 600 nm and 1300 nm.

* * * * *